United States Patent [19]
Laverroux et al.

[11] Patent Number: 6,164,105
[45] Date of Patent: Dec. 26, 2000

[54] METHOD AND DEVICE FOR MEASURING A MECHANICAL CHARACTERISTIC OF A LONG METALLIC PRODUCT METHOD OF CONTINUOUSLY PRODUCING A LONG PRODUCT, AND PRODUCT OBTAINED

[75] Inventors: Michel Laverroux, Savigny sur Orge; Pierre Megel, Sauvigny les Bois, both of France

[73] Assignee: Sprint Metal-Societe de Production Internationale de Trefiles, Puteaux, France

[21] Appl. No.: 09/260,010

[22] Filed: Mar. 2, 1999

[30] Foreign Application Priority Data

Mar. 5, 1998 [FR] France ................... 98 02722

[51] Int. Cl.⁷ .............................. B21C 9/00
[52] U.S. Cl. .................. 72/15.3; 72/286; 324/701
[58] Field of Search .................. 72/15.3, 16.2, 72/17.3, 286; 324/701

[56] References Cited

U.S. PATENT DOCUMENTS

| | | | |
|---|---|---|---|
| 2,186,826 | 1/1940 | Edgar | 324/701 |
| 2,580,670 | 1/1952 | Gilbert | 324/701 |
| 3,646,789 | 3/1972 | Forster . | |
| 4,545,227 | 10/1985 | Sudoh | 72/17.3 |

FOREIGN PATENT DOCUMENTS

| | | |
|---|---|---|
| 0 445 983 A2 | 9/1991 | France . |
| 2193810 | 2/1988 | United Kingdom . |

*Primary Examiner*—Daniel C. Crane
*Attorney, Agent, or Firm*—Oblon, Spivak, McClelland, Maier & Neustadt, P.C.

[57] ABSTRACT

Measurement of a mechanical characteristic of a long metallic product. The long product is passed through at least one turn of an electromagnetic coil energized with a variable current, the impedance of the electromagnetic coil is measured continuously and the mechanical characteristic of the long product or variations therein are determined by comparing the measured impedance with at least one predetermined impedance value. The method can be used in particular to regulate the production of hyperquenched austenitic steel spring wire containing martensite ($\alpha'$) by drawing the wire through successive dies. The impedance of the coil through which the wire passes when it leaves the die is measured in order to regulate at least one of the following parameters: the temperature of the die and the wire and the wire speed.

12 Claims, 2 Drawing Sheets

METHOD AND DEVICE FOR MEASURING A MECHANICAL CHARACTERISTIC OF A LONG METALLIC PRODUCT METHOD OF CONTINUOUSLY PRODUCING A LONG PRODUCT, AND PRODUCT OBTAINED

BACKGROUND OF THE INVENTION

1. Field of the Invention

The present invention relates to a method and a device for measuring a mechanical characteristic of a long metal product, a method of continuously producing a long product and the long product obtained. The invention applies in particular to the manufacture of long steel rods and wires having round or other shaped cross-sections.

2. Discussion of the Background

Manufacturing long products such as wires or small section rods is known per se. For example, a method of rolling or drawing is known, in which the long product moves continuously through the rolling or drawing installation to the exit from the installation where the long product can be wound, for example into the form of a spool or a coil, or is in the form of a rod.

Flat products such as strips can also be manufactured continuously, for example by rolling. Although such products are not usually designated long products, this term as used hereinafter refers equally to narrow flat products to which the invention is applicable.

Manufacturing austenitic steel wires of precisely specified diameter by drawing a machine wire or a rod through one or more successive dies of decreasing diameter to reduce its diameter is known. Traction is applied to the wire on leaving each die by a capstan. The wire may undergo the various drawing operations in a totally continuous manner by passing successively through the dies or in a series of steps after each of which an intermediate product is obtained that is drawn to a smaller diameter.

Manufacturing by drawing austenitic stainless steel wires where the metastable austenite is converted partly or totally into martensite because of plastic deformation is also known. Such wires, the tensile strength of which can be as high as around 2000 MPa, have various uses and in particular can be used to manufacture springs.

Wires of this type, obtained in the form of a spool or a coil after the drawing operation, have mechanical characteristics that depend not only on the chemical composition of the steel but also on the drawing conditions. To guarantee highly regular mechanical characteristics of the wire, the sample on which tensile tests are carried out is taken from the end of each spool or coil or from a wire portion obtained by means of a test drawing operation. The drawing conditions, and in particular the drawing speed, are adjusted in the light of the results of such tests either for a series of spools or for each spool. This procedure, possibly complemented by a final sorting of the spools or coils, guarantees that the tensile strength obtained is in a range of 100 MPa around the target value. This range, generally accepted and imposed by the usual standards, is sometimes deemed to be too high, and it is desirable to reduce it. The only known way of doing so is a more severe sorting than is usually practiced.

When such wires are used to manufacture coil springs, the geometry of the springs obtained is found to vary, not only when the wire is taken from different spools or coils but also when it is taken from the same spool or coil. It is then necessary to sort the springs and to reject those that do not have a satisfactory geometry.

SUMMARY OF THE INVENTION

The aim of the present invention is to overcome this drawback by drawing austenitic steel wires in which the austenite can be converted partly or totally into martensite by plastic deformation and manufacturing coil springs with a low range of characteristics without any sorting being needed.

To this end, the invention includes means for continuously measuring the mechanical characteristics of a long product, where the long product is passed through at least one turn of an electromagnetic coil energized with a varying current. The impedance of the electromagnetic coil is measured continuously and the mechanical characteristic of the long product or variations therein are determined by comparing the measured impedance with at least one predetermined impedance value.

The means for continuously measuring the mechanical characteristics of a long product can be disposed at the exit from a tool which shapes by plastic deformation, for example at the exit from a wire drawing die. The measurement obtained can be used in particular for continuous regulation of the shaping conditions, for example the drawing conditions. In this way it is possible to obtain long products whose mechanical characteristics inherently have a small range of values and in particular wires with a target tensile strength of approximately 2000 MPa with a measured tensile strength range of 20 MPa. When wires of the above kind are used to manufacture springs, it is no longer essential to sort the springs to obtain consistent batches of springs.

Moreover, if a calibration is carried out before drawing a wire of a given composition by comparing the measurements obtained in accordance with the invention, it is possible not only to improve the regularity of production but also to reduce the range of the mechanical characteristics obtained relative to the target value without the necessity of more test drawing operations and sorting of spools.

BRIEF DESCRIPTION OF THE DRAWINGS

To explain the invention, one embodiment of the invention applied to the regulation of a wire drawing line for an austenitic stainless steel spring wire will now be described by way of example and with reference to the accompanying drawings.

DETAILED DESCRIPTION OF THE PREFERRED EMBODIMENTS

Figure 1:
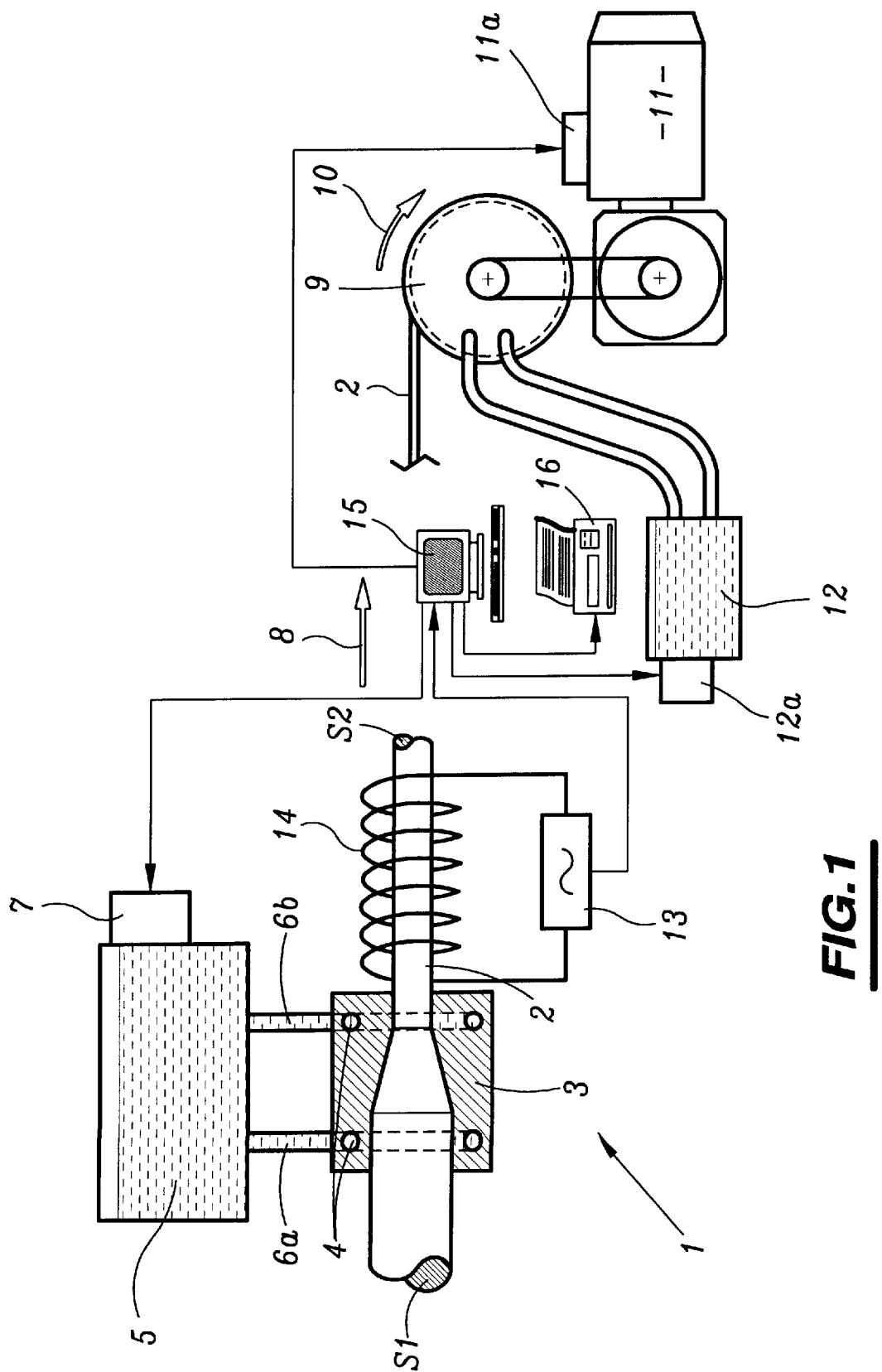
FIG. 1 is a partial diagrammatic view of a wire drawing installation and means for adjusting the drawing line on the basis of a continuous measurement carried out in accordance with the invention.

Referring now to the drawings, wherein like reference numerals designate identical or corresponding parts throughout the several views, FIG. 1 is a diagram showing a wire drawing installation 1. The wire drawing installation 1 includes a number of dies in succession along the path of the wire 2 during the drawing operation. For simplicity, only one die 3 is shown in which the section of the wire 2 is reduced from a value S1 to a value S2, the ratio S1/S2 constituting the reduction ratio through the die 3.

The wire 2, the diameter of which is reduced in the successive dies like die 3, is an austenitic stainless steel wire, for example a spring steel wire, having the following composition (percentages by weight):

| C | Si | Mn | Ni | Cr | N |
|---|---|---|---|---|---|
| 0.08 | 0.8 | 1 | 8.5 | 18 | 0.04 | and a dynamic martensitic transformation point Md on the order of 15° C.

The steel, cast in the form an ingot or billet, is converted by rolling into a machine wire having a diameter greater than or equal to 5 mm. The machine wire is hyperquenched from a temperature of 1050° C. and then drawn to a diameter of 0.15 mm in the wire drawing installation. The target tensile strength for the wire on leaving the drawing installation is approximately 2000 MPa.

The wire 2 in contact with the die 3 is heated from a temperature in the range 20° C. to 50° C. to a temperature which can be as high as several hundred degrees. To remove the heat and to limit the heating of the wire, the die 3 includes a cooling circuit 4 which can be internal to the die and consists in a passage for water to flow in, or external to the die and consists in a cooling coil. The cooling circuit 4 of the die 3 is fed with cooling fluid at a controlled temperature by a cooling fluid supply 5 via a pipe 6a feeding the circuit of the die. A return pipe 6b returns the cooling fluid to the supply 5, which is-controlled by a control unit 7. The control unit 7 of the cooling fluid supply 5 adjusts the flowrate of the cooling fluid sent to the cooling circuit 4 of the die and the temperature of the cooling fluid.

As shown by the arrow 8, the wire 2 is drawn through the die 3 by a capstan 9 rotating in the direction indicated by the arrow 10 and applying traction to the end of the wire 2 leaving the die 3. The capstan 9 is rotated by a variable speed motor 11 associated with a speed adjuster device 11a. The capstan 9 can be cooled by a cooling circuit 12 to control the temperature of the wire leaving the installation or in an intermediate step with a second drawing step.

By controlling the rate with which the die 3 is cooled, the speed of the wire imposed by the capstan 9 and the wire exit temperature, it is possible to adjust the tensile mechanical characteristics of the wire obtained and in particular its tensile strength.

To this end, the cooling water supply 5 of the die 3 and the speed imposed by the capstan 9 can be precisely adjusted by measuring the tensile strength of the wire as it leaves the die 3 or a set of dies.

In accordance with the invention, on leaving the die 3, the wire passes through a means for continuously measuring the mechanical characteristics of the wire, described hereinafter. This measurement, or the result of comparing it with a set point value, is used to continuously regulate the cooling of the die 3 and the speed imposed by the capstan 9, the cooling of which can also be regulated. In this way the mechanical characteristics of the wire are continuously regulated. These characteristics depend not only on the work hardening rate, which is set by the entry diameter of the wire and by the diameter of the die, but also on the temperature at which work hardening is effected. The temperature at which work hardening is effected is directly dependent on the temperature of the die and on the drawing speed. This temperature also depends on the temperature of the wire entering the die. When there is only one die, this temperature is ambient temperature, with variations which are generally negligible. When drawing is effected by passing the wire through successive dies, the entry temperature into one die can be regulated by varying the cooling of the capstan associated with the previous die.

The mechanical characteristics of the wire are measured continuously by a method using Eddy currents. It consists of continuously measuring the impedance of an electromagnetic coil energized by an alternating current through which the drawn wire passes. This measurement, the conditions for which are described hereinafter, is carried out in such a manner as to eliminate disturbances caused by wire surface defects.

Although we know that it is possible to use a magnetic method to evaluate the martensite content of an austenitic stainless steel drawn wire in which the austenite is metastable, the inventors have found, unexpectedly, that for a given chemical analysis of the steel there is a close correlation between the magnetic measurement and the mechanical characteristics of the wire. A measuring method using eddy currents as described hereinafter provides a sufficiently precise and responsive continuous measurement of the mechanical characteristics for effective and continuous regulation of the mechanical characteristics of the wire during drawing.

What is more, by carrying out calibration beforehand, it is possible to not only apply regulation to assure constant mechanical characteristics of the wire throughout the same spool but also so that the mechanical characteristics are as close as possible to the target values.

To carry out such calibration, a series of magnetic measurements and tensile tests are carried out on wires having the same chemical composition and the same diameter but corresponding to different degrees of work hardening or different work hardening conditions, and having different martensite contents. All of the data collected in this way is used to establish the relationship between the magnetic measurement and the mechanical characteristics. The inventors have also found, surprisingly, that this relationship is virtually linear for martensite content in the range of from practically 0% to practically 100%, for example from 5% to 95%.

In order to obtain not only constant mechanical characteristics all along the wire but also characteristics as close as possible to the target values, it is sufficient to regulate about a value of the magnetic measurement deduced from the calibration curve.

In accordance with the invention, the wire 2 leaving the die 3 passes through the turns of an electromagnetic coil 14 energized with a varying current by a variable current supply 13 connected to a unit 15 for controlling the electrical power supply and for processing a variable signal from the coil 14. The unit 15 measures the impedance of the electromagnetic coil 14 through the turns of which the wire 2 passes and compares the impedance to set point values.

The processor unit 15 is preferably a microcomputer connected to a measurement result display device 16. The processor unit 15 is also connected to the module 7 for controlling the cooling water supply 5 of the die, to the module 11a for controlling the speed of the motor 11 of the capstan 9 and to the module 12a for controlling the cooling circuit 12 of the capstan.

In the case of the coil 14 shown in FIG. 1 through which the moving wire 2 passes along its axis, the impedance of the coil 14 depends on the currents induced by the varying current in the wire 2 of the coil. The induced currents depend in turn on the magnetic properties of the material of the wire 2.

The absolute value of the impedance of the coil 14 can be written:

$$|Z_1| = \sqrt{R_1^2 + L_1^2 \omega^2}$$

where R and L are respectively the resistance and the inductance of the electromagnetic coil and ω is the varying angular frequency of the current.

The inductance L of the electromagnetic coil depends on the magnetic permeability μ of the core consisting of the moving wire 2 inside the turns of the coil. Because the wire 2 is made of a non-magnetic austenitic stainless steel containing a certain proportion of ferromagnetic martensite, the magnetic permeability 11 varies with the proportion of martensite in the wire 2.

During wire drawing in the installation shown in FIG. 1, the voltage across the electromagnetic coil 14 and the current measured by the units 13 and 15 determine the impedance of the electromagnetic coil.

In reality, as explained hereinafter, measurement or comparison methods employing a measurement bridge are generally employed. The impedance is then automatically compared with a bridge balancing impedance fixed at the outset.

The impedance values determined by the processor unit 15 can be compared to calibration values previously supplied to the processor unit 15. Values of the tensile strength and/or of the elastic limit are obtained which can be displayed in any form or printed out at the display device 16 connected to the processor unit 15.

Also, the measured impedance signals or signals corresponding to the value of the tensile strength are compared to a set point value corresponding to the required tensile strength of the wire as it leaves the die 3.

Depending on the measured difference between the continuously measured value and the set point value, control signals are transmitted to the module 7. The module controls the cooling water supply 5 of the die 3 and/or the control module 11a of the motor 11 of the capstan 9 which varies the cooling of the die 3 by varying the flowrate and/or the temperature of the cooling water from the cooling supply 5 and the temperature of the wire at the die and/or the speed of the wire. This control cancels out the difference between the measured impedance or tensile strength and the set point value. The flowrate and the temperature of the water from the cooling circuit of the capstan 9 can equally be regulated in accordance with the measured impedance.

Because of the close correlation between the tensile strength of the wire and the impedance of the coil, the value of the tensile strength as it leaves the die 3 can be controlled with great accuracy, which was entirely impossible with the prior art processes.

Figure 2:
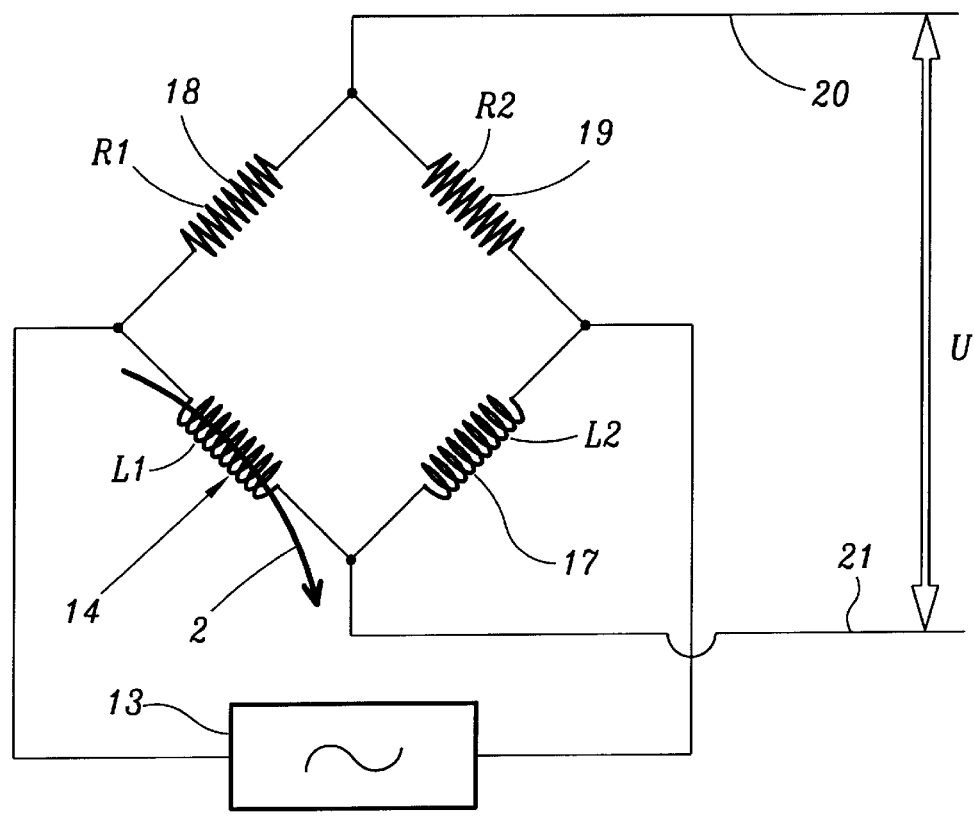
FIG. 2 is a diagrammatic view of one embodiment, in the form of a bridge, of means for monitoring variations in the impedance of the electromagnetic coil while the wire is passing through it.

The wire drawing installation is preferably controlled using a bridge, one branch of which is the electromagnetic coil 14 with the wire 2 passing through it, as shown in FIG. 2. The measuring bridge has a second branch consisting of a second electromagnetic coil 17, a third branch consisting of a first electrical resistor 18 and a fourth branch consisting of a second electrical resistor 19.

The power supply unit 13 supplying the high frequency current is connected between the point common to the first and third branches and the point common to the second and fourth branches of the bridge. The bridge imbalance signal is the voltage signal or the current between the point common to the first and second branches and the point common to the third and fourth branches of the bridge.

The bridge is balanced for a value of the impedance of the electromagnetic coil 14 corresponding to the presence of a wire 2 in the coil, the tensile strength of which is equal to the set point tensile strength of the wire after drawing.

Note that the impedance of the electromagnetic coil 14 and therefore the measurement or the adjustment carried out do not depend on the position of the wire inside the turns of the coil 14 so that the measurements or the regulation are not disturbed or subject to error in any way if the wire is not precisely aligned with the axis of the coil.

Imbalance of the bridge detected in the form of a current or a voltage between the measuring branches 20 and 21 is the result of the difference between the impedance $Z_1$ of the first and third branches 14 and 18 and the impedance $Z_2$ of the second and fourth branches 17 and 19 in series with each other.

Let R1 and R2 denote the values of the resistors 18 and 19, respectively, and L1 and L2 denote the inductances of the coils 14 and 17, respectively. The absolute values of the impedances $Z_1$ and $Z_2$ and the difference between them can be expressed as follows:

$$|Z_1| = \sqrt{R_1^2 + L_1^2 \omega^2}$$
$$|Z_2| = \sqrt{R_2^2 + L_2^2 \omega^2}$$
$$|Z_1| - |Z_2| = \sqrt{R_1^2 + L_1^2 \omega^2} - \sqrt{R_2^2 + L_2^2}\,\omega^2$$

The imbalance of the bridge that is detected yields the difference between the impedances $Z_1$ and $Z_2$.

The difference between the absolute values of the impedances $Z_1$ and $Z_2$ is a function of the angular frequency ω of the energization current, which can be graphically represented by a curve.

To be able to carry out the measurements on a practically linear portion of the curve and to cancel out the phase difference between the impedances $Z_1$ and $Z_2$, the resistor R1 is adjusted in accordance with the angular frequency ω of the coil energization current.

To this end, the resistor R1 in the third branch 18 of the bridge is a variable resistor, of the rheostat type, controlled in accordance with the frequency of the current from the power supply 13.

Figure 3:
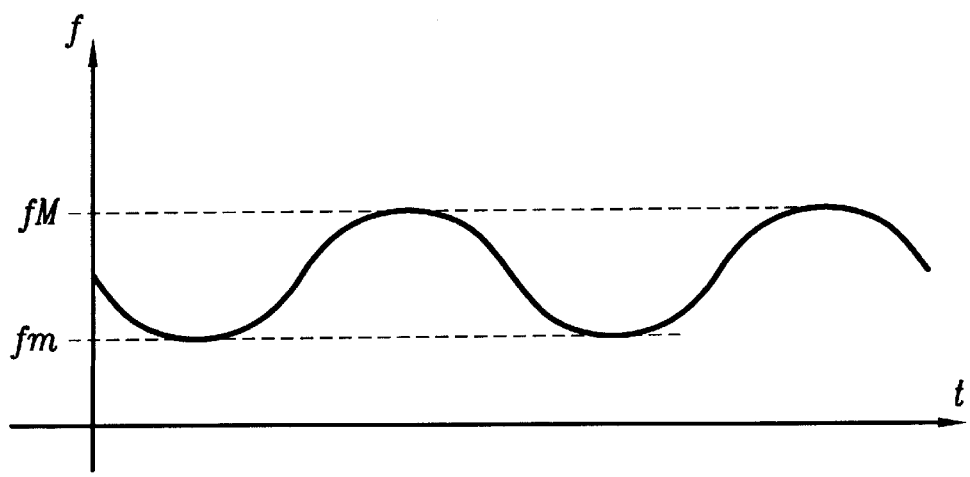
FIG. 3 is a diagram showing the variation in the frequency of the electromagnetic coil excitation current as a function of time.

As can be seen in FIG. 3, the power supply current of the bridge shown in FIG. 2, or of the coil shown in FIG. 1, is a modulated frequency current. The frequency varies periodically with time between a minimum value fm and a maximum value fM selected in accordance with the diameter of the wire which is being measured, or more generally in accordance with the dimension of the section of the long product in the measuring area.

The frequency fm is generally in the range 40 kHz to 50 kHz and the frequency fM is generally in the range 200 kHz to 300 kHz. The periodically modulated frequency varies the penetration of current into the wire between a very thin surface layer for the maximum frequency fM and the whole section of the wire for the minimum frequency fm.

The bridge imbalance signal (or the impedance signal) is integrated over a time period corresponding to a whole number of frequency variation periods. This eliminates the disturbing effects of wire surface defects, which can be conventionally detected by "eddy current" methods, by specific processing of the signal.

The resistor R1 is a rheostat type variable resistor and a variable inductor with a moving core is disposed in series with the coil 14 in the corresponding branch of the bridge. In this way, the bridge can be balanced so that the imbalanced signal can be used as a set point value controlling the wire drawing installation, as described hereinabove.

The invention can in particular provide surface hardened and hyperquenched austenitic stainless steel wire with an ultimate tensile strength on the order of 2000 MPa with an accuracy better than 20 MPa throughout the length of the wire produced continuously in a wire drawing installation. More generally it can provide a variation less than 1% in the tensile strength of the wire along its length in wires having a diameter in the range 0.1 mm to 20 mm and preferably in the range 0.15 mm to 2.5 mm.

The wires obtained have the advantage of enabling mass production of springs with characteristics that show little spread. The inventors have found, unexpectedly, that the problems encountered in the manufacture of springs from prior art wires resulted in particular from the lack of regularity of the mechanical characteristics in wire from the same spool.

The measuring method in accordance with the invention can equally be used to measure the tensile strength and/or the elastic limit of long products other than spring wires, for example austenitic steel wires or rods for the manufacture of cables, screws, bolts, pins, hooks, woven wire or braiding. In all cases, hyperquenched austenitic stainless steel wires or bars, in which the content of martensite $\alpha'$ is in the range of from practically 0% to practically 100%, can be obtained continuously with tensile mechanical characteristics such that the ultimate tensile strength and the elastic limit are constant to within better than 1%.

The invention can equally be used to adjust the rolling of narrow strip so that the strip has tensile mechanical characteristics that are perfectly constant throughout its length. In this case the moving strip is passed through an electromagnetic coil of flatter section.

The invention is not limited to the embodiments that have been described. Any impedance measuring method or device can be used to determine the impedance of the electromagnetic coil through which the moving long product passes.

The impedance or impedance variation measurements obtained or the imbalance signal from a measuring bridge can be used to supply values of the tensile strength or of the elastic limit of the long product or to regulate an installation for manufacturing the long product by mechanical conversion, for example by wire drawing and/or rolling.

The invention applies generally to round or other profile wires, and more generally to long products, made of alloys having a metastable non-magnetic phase that can be partly or totally converted to a magnetic phase by work hardening. This is the case, in particular, for austenitic steels in which the austenite is metastable at ambient temperature, whether such steels are stainless steels or otherwise, and whether they primarily contain nickel or manganese in addition to iron. This is the case, in particular, for austenitic spring steels which contain, by weight, 6% to 12% nickel, 16% to 20% chromium, at most 0.15% carbon, at most 0.15% nitrogen, 0% to 2% silicon and 0% to 2% manganese, the remainder being iron and impurities due to manufacture. The steel can further contain small quantities of complementary alloying elements.

The invention applies equally to long products made of manganese austenitic steel or austenitic steel containing molybdenum, cobalt or other alloying elements.

If the long product is a cold rolled strip, the rolling conditions can be regulated by operating on the lubrication and on the rolling speed in particular.

Obviously, numerous modifications and variations of the present invention are possible in light of the above teachings. It is therefore to be understood that within the scope of the appended claims, the invention may be practiced otherwise than as specifically described herein.

We claim:

1. Method of continuously measuring a mechanical characteristic of a long product of hyperquenched austenitic steel containing martensite with the long product in motion, comprising the steps of:
   passing the long product through at least one turn of an electromagnetic coil which is energized with a variable current;
   measuring a measured impedance of the electromagnet coil continuously; and
   determining the mechanical characteristic of the long product by comparing the measured impedance with at least one predetermined impedance value deduced from a calibration curve giving a correlation between the measured impedance and the mechanical characteristic.

2. Method according to claim 1 wherein the ultimate tensile strength and/or the elastic limit of the long product is obtained from the measured impedance and from calibration values.

3. Method according to claim 1 wherein the electromagnetic coil is energised with an alternating current the frequency of which is modulated and varies periodically with time between a minimum value and a maximum value.

4. Method according to claim 3 wherein the minimum frequency and the maximum frequency are chosen in accordance with the dimension of the section of the long product and the minimum frequency is in the range 40 kHz to 50 kHz and the maximum frequency in the range 200 kHz to 300 kHz.

5. A measuring device for continuously measuring a mechanical characteristic of a long product of hyperquenched austenitic steel containing martensite with the long product in motion, comprising:
   an electromagnetic coil disposed so that the moving long product passes through turns of said coil;
   a variable current power supply unit energizing the coil with a variable current;
   means for measuring a measured impedance of the electromagnetic coil;
   means for comparing the measured impedance with calibration values to obtain mechanical characteristic values; and
   means for displaying values of the mechanical characteristic obtained by comparison,
   wherein the variable current power supply unit comprises a variable frequency alternating current power supply unit outputting said variable current with a frequency modulated between a minimum value and a maximum value.

6. Device for continuously measuring a mechanical characteristic of a long product of hyperquenched austenitic steel containing martensite with the long product in motion, comprising:
   an electromagnetic coil through which passes said product;
   a variable power supply providing variable current to energize said coil;
   means for measuring an impedance of the electromagnetic coil continuously using a bridge;
   means for determining the mechanical characteristic of the long product by comparing the measured impedance with at least one predetermined impedance value;
   wherein the electromagnetic coil through which the long product is passed is a first branch of said bridge; a second branch of said bridge is an electromagnetic coil in series with the first branch; a third branch is an electrical resistor in series with the first branch; a fourth branch is an electrical resistor in series with the second and third branches of the bridge; and said variable power supply being connected between a point common to the first and third branches and a point common to the second and fourth branches of the bridge;

a branch imbalance current or voltage being measured between a point common to the first and second branches of the bridge and a point common to the third and fourth branches of the bridge to determine variations in the impedance of the electromagnetic coil constituting the first branch of the bridge.

7. Device according to claim 6 wherein the resistor constituting the third branch of the bridge is a variable resistor controlled in accordance with the frequency of the current energising the electromagnetic coil.

8. Method of continuously producing a long product of hyperquenched austenitic stainless steel, comprising the steps of:

passing the long product through at least one die to reduce a section of the long product;

applying traction to the long product by means of a capstan;

providing the die with a cooling circuit supplied by a cooling water supply;

driving the capstan by a variable speed motor associated with a unit for varying the speed of the motor;

after passing through at least one die, passing the product through an electromagnetic coil energized with a variable current;

measuring the impedance of the coil through which the long product is moving; and regulating according to the measured value of the impedance of the electromagnetic coil at least one of a flowrate of cooling water from the cooling water supply to the die, a temperature of the cooling water from the cooling water supply and the speed of the drive motor of the capstan.

9. Method according to claim 8, wherein the capstan is cooled by a cooling circuit circulating cooling water in the capstan, and a flowrate and temperature of the water in the cooling circuit of the capstan are regulated in accordance with the measured impedance of the electromagnetic coil.

10. A measuring device configured to continuously measure a mechanical characteristic of a long product of hyperquenched austenitic steel containing martensite with the long product in motion, comprising:

an electromagnetic coil disposed so that the moving long product passes through turns of said coil;

a variable current power supply unit energizing the coil with a variable current;

a measurement device configured to measure a measured impedance of the electromagnetic coil;

a comparison device configured to compare the measured impedance with calibration values to obtain mechanical characteristic values; and a display configured to display values of the mechanical characteristic obtained by comparison, wherein the variable current power supply unit comprises a variable frequency alternating current power supply unit outputting said variable current with a frequency between a minimum value and a maximum value.

11. A device configured to continuously measure a mechanical characteristic of a long product of hyperquenched austenitic steel containing martensite with the long product in motion, comprising:

an electromagnetic coil through which passes said product;

a variable current power supply unit providing a variable current to energize said coil:

a measurement device configured to measure a measured impedance of the electromagnetic coil continuously using a bridge;

a mechanism configured to determine the mechanical characteristic of the long product by comparing the measured impedance with at least one predetermined impedance value;

wherein the electromagnetic coil through which the long product is passed comprises a first branch of said bridge, a second branch of said bridge comprises an electromagnetic coil in series with the first branch, a third branch comprises a first electrical resistor in series with the first branch, a fourth branch comprises a second electrical resistor in series with the second and third branches of the bridge, said variable power supply being connected between a point common to the first and third branches and a point common to the second and fourth branches of the bridge, and at least one of a branch imbalance current and a voltage is measured between a point common to the first and second branches of the bridge and a point common to the third and fourth branches of the bridge to determine variations in the impedance of the electromagnetic coil constituting the first branch of the bridge.

12. The device according to claim 11 wherein the first electrical resistor comprises a variable resistor controlled in accordance with the frequency of the current energizing the electromagnetic coil.

* * * * *